US005880095A

United States Patent [19]

Park et al.

[11] Patent Number: 5,880,095

[45] Date of Patent: Mar. 9, 1999

[54] CHOLESTERYL ESTER TRANSFER PROTEIN INHIBITOR PEPTIDES AND PROPHYLACTIC AND THERAPEUTIC ANTI-ARTERIOSCLEROSIS AGENTS

[75] Inventors: Yong-Bok Park; Kyung-Hyun Cho, both of Taegu, Rep. of Korea

[73] Assignee: LG Chemical Ltd., Seoul, Rep. of Korea

[21] Appl. No.: 666,300

[22] PCT Filed: Nov. 13, 1995

[86] PCT No.: PCT/KR95/00148

§ 371 Date: Jun. 26, 1996

§ 102(e) Date: Jun. 26, 1996

[87] PCT Pub. No.: WO96/15141

PCT Pub. Date: May 23, 1996

[30] Foreign Application Priority Data

Nov. 12, 1994 [KR] Rep. of Korea ...................... 94-29713

[51] Int. Cl.$^{6}$ .......................... A61K 38/04; A61K 38/16; C07K 7/00; C07K 14/00

[52] U.S. Cl. ................................ 514/12; 515/13; 515/14; 515/15; 530/324; 530/325; 530/326; 530/327; 530/328; 424/803; 435/19

[58] Field of Search ............... 514/12–15; 530/324–328, 530/350, 364; 424/803; 435/19

[56] References Cited

U.S. PATENT DOCUMENTS 5,519,001 5/1996 Kushwaha et al. ........................ 514/12

OTHER PUBLICATIONS

Birchbauer et al., Genomics vol. 15 pp. 643–652 (1993).

Trieu et al., Gene vol. 123 pp. 173–179 (1993).

McCunathy et al. J. Lipid Res. vol. 33 (1992) pp. 995–1003.

*Primary Examiner*—Cecilia J. Tsang
*Assistant Examiner*—Bennett Celsa
*Attorney, Agent, or Firm*—Anderson, Kill & Olick, P.C.

[57] ABSTRACT

A peptide consisting of the following amino acid sequence, or an analogue or a fragment thereof, has an inhibitory activity on cholesteryl ester transfer protein:

Glu Asp Thr Ser Pro Glu Asp Lys Met Gln Asp Tyr Val Lys Gln Ala Thr Arg Thr Ala Gln Asp Ala Leu Thr Ser Val Lys.

8 Claims, 10 Drawing Sheets

CE: cholesteryl ester
TG: triglyceride
PC: phosphatidylcholine

CHOLESTERYL ESTER TRANSFER PROTEIN INHIBITOR PEPTIDES AND PROPHYLACTIC AND THERAPEUTIC ANTI-ARTERIOSCLEROSIS AGENTS

This application is a 371 of PCT/KR95/00148 filed Nov. 13, 1995, published as WO96/15141 May 23, 1996.

FIELD OF THE INVENTION

The present invention relates to novel cholesteryl ester transfer protein(CETP) inhibitor peptides and prophylactic and therapeutic anti-arteriosclerosis agents comprising same.

BACKGROUND OF THE INVENTION

Arteriosclerosis is one of the diseases suffered by an increasing population of adults and even adolescents and children, often caused by dietary changes.

While a number of risk factors, either genetic or environmental, for the attack and progress of arteriosclerosis have been reported, recent studies have singled out elevated plasma cholesterol levels as a primary risk factor. Therefore, a great deal of attention has been devoted to the establishment of relationships between the level of blood lipoproteins or lipids and the risk of developing a coronary heart disease. As is well known, both high density lipoproteins(HDL) and low density lipoproteins(LDL) carry cholesterol in human blood mainly in the form of cholesteryl esters(CE). Specifically, HDL serves to transport cholesterol that remains in peripheral cells back to the liver, where cholesterol is decomposed and eliminated. Since, therefore, cholesterol can be easily eliminated when it is carried by HDL, plasma cholesterol levels can be effectively decreased by blocking the transfer of cholesterol from HDL to other lipoproteins.

In this connection, CETP transfers CE from HDL to LDL or very low density lipoproteins(VLDL); and there have been extensive studies on its function. For instance, Drayna et al. have determined the cDNA sequence of human CETP and successfully cloned it(*Nature*, 327, 6123(1987)); and Wang et al. have reported the production of human CETP using a vector comprising cDNA of human CETP(*DNA*, 8, 753–758(1989)).

Kushwaha et al. have reported that several species of animals which lack CETP have high HDL-cholesterol levels and low LDL-cholesterol levels, and, further, show a low rate of arteriosclerosis attack(*J. of Lipid Research*, 34, 1285–1297(1993)). This fact suggests an important interrelationship among CETP, cholesterol levels and attack of arteriosclerosis.

Further, familial members lacking CETP in Japan have been reported to have large HDL particles and to live long without occurrences of heart diseases(Koizumi et al., *Arteriosclerosis*, 58, 175–186(1986)). Recently, Marotti et al. have reported that when mice lacking CETP were transformed with a heterogenous CETP gene, serious arteriosclerosis occurred in transgenic mice in comparison with a reference mouse group(*Nature*, 364, 73—73(1986)).

These observations tend to support the hypothesis that, if CETP is made deficient or its activity is inhibited, transfer or elimination of cholesterol through HDL will be promoted, thereby rendering it possible to prevent or treat diseases caused by high levels of cholesterol, e.g., arteriosclerosis.

FIG. 1 shows a schematic view of the role of CETP and interrelationship between CETP and its inhibitor in the cholesterol reverse-transportation pathway. As shown in FIG. 1, cholesterol is carried by HDL in the form of CE, and transferred to LDL by CETP. CE in LDL is transferred to peripheral areas and accumulates in the cells, while CE in HDL is transported to the liver, where it is decomposed and eliminated.

When the amount of CE to be transported exceeds the transporting capacity of HDL, then CE becomes deposited in the cells in certain critical areas such as arterial walls. Such accumulation eventually results in impaired cell functions and, if continued, may cause cell death, which may, in turn, lead to the accumulation of cellular debris in the wall of blood vessels to induce atherosclerosis. In this case, however, if the action of CETP is inhibited or blocked, CE in HDL will not be transferred to LDL and will be transported to liver, thereby preventing or minimizing the accumulation of CE at, e.g., the wall of blood vessels, and the occurrence of arteriosclerosis.

In this context, many attempts have been made to inhibit or lower the CETP activity in order to lower the plasma cholesterol levels.

U.S. Pat. No. 5,279,540 discloses a method for lowering blood CETP concentration in an arteriosclerosis patient by passing the patient's blood through an anti-CETP column to treat arteriosclerosis.

PCT Publication No. WO 93/11782 discloses a peptide which is separated from the blood plasma of baboon and has a CETP inhibiting activity; amino acid sequence thereof; and a synthetic peptide prepared on the basis of said sequence which has a CETP inhibiting activity equal to that of natural one.

However, there still exists a need for a CETP inhibitor peptide having an excellent CETP inhibiting activity.

SUMMARY OF THE INVENTION

Accordingly, it is an object of the present invention to provide a novel CETP inhibitor peptide having an excellent inhibiting activity.

Another object of the present invention is to provide a process for preparing said peptide.

A further object of the present invention is to provide prophylactic and therapeutic anti-arteriosclerosis agents comprising said peptide.

In accordance with one embodiment of the present invention, there is provided a novel CETP inhibitor peptide, Peptide $P_{28}$, having the amino acid sequence of:

Glu Asp Thr Ser Pro Glu Asp Lys Met Gln Asp Tyr Val Lys Gln Ala Thr Arg Thr Ala Gln Asp Ala Leu Thr Ser Val Lys . . . (SEQ ID NO: 1)

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1:
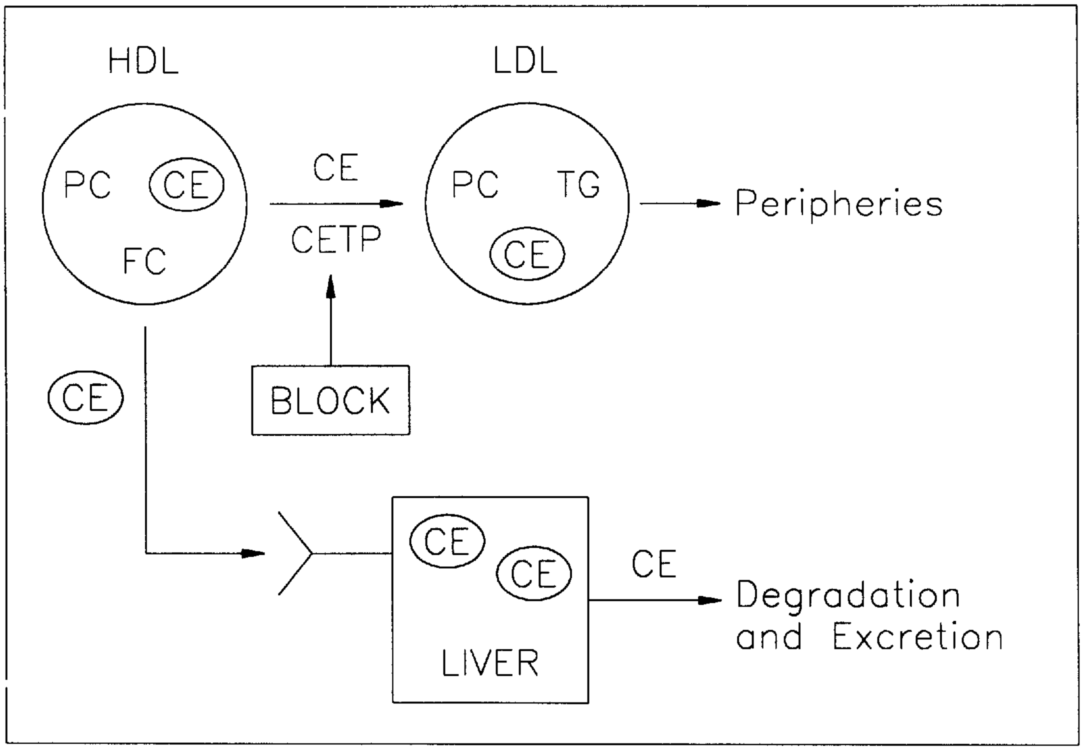
FIG. 1 shows a schematic illustration of the role of CETP and interrelationship between CETP and its inhibitor in the cholesterol reverse-transportation pathway.

The CETP inhibitor peptide of the present invention, i.e., Peptide $P_{28}$, has a molecular weight of about 3 kDa, which is confirmed by a polyacrylamide gel electrophoresis, and exhibits a high CETP inhibitory activity in in vitro tests, i.e., about 90–100% against pure CETP and about 4–50% against human blood plasma.

When the amino acid sequence of Peptide $P_{28}$, is compared with those of other peptides deposited at an amino acid data bank(i.e., KRIBB of KIST, Korea), the result shows that the amino acid sequence of Peptide $P_{28}$ is very similar to that of the N-terminal fragment of porcine apo-CIII protein, i.e., Peptide $P_{28'}$, which includes 28 amino acids as shown below:

Glu Asp Thr Ser Leu Leu Asp Lys Met Gln Asp Tyr Val Lys Gln Ala Thr Arg Thr Ala Gln Asp Ala Leu Thr Ser Val Lys . . . (SEQ ID NO: 2)

Porcine apo-CIII consists of 73 amino acids and is mainly synthesized in liver and, a small amount, in the small intestine. There is no report on the function of apo-CIII, but it is known to be one of trace proteins consisting of VLDL and HDL.

As shown above, amino acid sequences of Peptides $P_{28}$ and $P_{28'}$ are the same, except that the 5th and 6th amino acids from the N-terminal are different with each other. Peptide $P_{28'}$ also exhibits a CETP inhibitory activity of about 90–100% against pure CETP and about 40–50% against human blood plasma.

The Peptides $P_{28}$ and $P_{28'}$ may be prepared by separating them from porcine blood plasma using various column chromatographic techniques, or by synthesizing a peptide having the same amino acid sequences in accordance with known chemical methods. The chemically-synthesized peptides show CETP inhibitory activities essentially equal to those of the natural ones.

Further, human apo-CIII is a glycoprotein consisting of 79 amino acids wherein a carbohydrate moiety is bound to the 74th amino acid. It has a molecular weight of 8.7 kDa and inhibits the a activity of lipoprotein lipase and hepatic lipase. The N-terminal fragment of human apo-CIII protein, i.e., Peptide $P_{13}$, which comprises the following 13 amino acids, also exhibits a CETP inhibitory activity:

Ser Glu Ala Glu Asp Ala Ser Leu Leu Ser Phe Met Gln . . . (SEQ ID NO : 3)

Fragments of Peptides $P_{28}$, $P_{28'}$ and $P_{13}$ also exhibit the CETP inhibitory activities. Exemplary fragments thereof include N-terminal fragments of Peptide $P_{28}$ having the 1st to 10th($P_{10}$), 1st to 24th($P_{24}$), 1st to 20th($P_{20}$), 1st to 14th($P_{14}$), or 1st to 8th amino acids($P_8$); and of Peptide $P_{28'}$, having the 1st to 18th amino acids($P_{18}$) whose amino acid sequences are as follows:

$P_{10}$:

Glu Asp Thr Ser Pro Glu Asp Lys Met Gln . . . (SEQ ID NO: 4)

$P_{18}$:

Glu Asp Thr Ser Leu Leu Asp Lys Met Gln Asp Tyr Val Lys Gln Ala Thr Arg . . . (SEQ ID NO: 5)

$P_{24}$:

Glu Asp Thr Ser Pro Glu Asp Lys Met Gln Asp Tyr Val Lys Gln Ala Thr Arg Thr Ala Gln Asp Ala Leu . . . (SEQ ID NO: 6)

$P_{20}$:

Glu Asp Thr Ser Pro Glu Asp Lys Met Gln Asp Tyr Val Lys Gln Ala Thr Arg Thr Ala . . . (SEQ ID NO: 7)

$P_{14}$:

Glu Asp Thr Ser Pro Glu Asp Lys Met Gln Asp Tyr Val Lys . . . (SEQ ID NO: 8)

$P_8$:

Glu Asp Thr Ser Pro Glu Asp Lys . . . (SEQ ID NO: 9)

Variants of Peptides $P_{28}$, $P_{28'}$, $P_{13}$, $P_{10}$, $P_{24}$, $P_{20}$, $P_{14}$, or $P_{18}$ and fragments thereof having CETP inhibitory activity, which have at least one amino acid substitution by a known modified amino acid while maintaining their CETP inhibitory activity, are also included within the scope of the present invention. The substitute amino acids may be selected from the group consisting of:

2-amino adipic acid, Asp or $C_a$-methylGlu for Glu;

Glu, $C_a$-methylAsp or β-carboxyAsp for Asp;

Ser or $C_a$-methylThr for Thr;

Thr or $C_a$-methylSer for Ser;

3,4-dehydroPro or $C_a$-methylPro for Pro;

ornithine, citrulline, Arg or $C_a$-methylLys for Lys;

$C_a$-methylMet for Met;

Asn, citrulline or $C_a$-methylGln for Gln;

isoVal, norval, $C_a$-methylVal or Leu for Val;

Gly, β-Ala, $C_a$-methylAla or 2-aminobutyric acid for Ala;

Lys, homoArg, $C_a$-methylArg or citrulline for Arg; and norLeu, isoLeu or $C_a$-methylLeu for Leu.

Further, peptide bonds in Peptides $P_{28}$, $P_{28'}$ and $P_{13}$, fragments thereof or their analogues may be replaced with other bonds, e.g., thioether bond(—$CH_2$—S—), alkyl bond (—$CH_2$—$CH_2$—) and amino bond(—$CH_2$—$NH_2$—).

Polypeptides or proteins, which comprise Peptide $P_{28}$, $P_{28'}$ or $P_{13}$ or a fragment thereof, may exhibit CETP inhibitory activities and are also included within the scope of the present invention.

Further, the present invention provides an antibody having a specificity for Peptide $P_{28}$, $P_{28'}$, or $P_{13}$, a fragment thereof or a polypeptide or protein comprising the above peptides. The antibodies of the present invention is useful for the preparation of prophylactic and diagnostic agents for arteriosclerosis.

The peptides of the present invention are inhibitors of CETP, which blocks the transfer of CE from HDL to LDL and VLDL, whereby CE is transferred to liver by HDL, and cholesterol in peripheral cells are removed. Accordingly, the CETP inhibitory peptides of the present invention may be used in the prophylaxis or treatment of arteriosclerosis.

Therefore, the present invention provides an anti-arteriosclerosis composition which comprises Peptide $P_{28}$, $P_{28'}$ or $P_{13}$, fragments thereof or its analogues as an active ingredient, in an amount effective for lowering the blood cholesterol level, or preventing or treating arteriosclerosis, in combination with a pharmaceutically acceptable excipients, carriers or diluents. The compositions may be prepared in accordance with any of the conventional procedures.

In preparing the compositions, the active ingredient is preferably admixed or diluted with a carrier, or enclosed within a carrier. Thus, the compositions may be in the form of a tablet, pill, powder, sachet, elixir, suspension, emulsion, solution, syrup, aerosol, soft or hard gelatin capsule, sterile injectable solution, sterile packaged powder, or the like, preferably, a sterile injectable solution. When the composition is prepared into an injectable solution, it can be stored or administered in a freeze-dried form.

Examples of suitable carriers, excipients, and diluents are starch, lactose, dextrose, sucrose, mannitol, calcium carbonate, dipotassium hydrogenphosphate, sodium chloride, microcrystalline cellulose, dextrin, sodium alginate, methyl cellulose, kaolin, colloidal silicon dioxide, hydroxypropyl starch, propylene glycol, casein, sodium hydrocarbonate, potassium lactate, potassium lactate, lanolin, gelatin, glycerin, bentonite, calcium stearate, polyvinylalcohol, sodium citrate, polyoxyethylene sorbitol, and lanolin ester.

The compositions may additionally include lubricating agents, wetting agents, flavoring agents, emulsifiers, suspending agents, stabilizers, binding agents, preservatives and the like. The compositions of the invention may be formulated so as to provide quick, sustained or delayed release of the active ingredient after their administration to a patient by employing any of the procedures well known in the art.

The pharmaceutical compositions can be administered daily or at a regular interval, by a variety of routes including oral, transdermal, subcutaneous, intravenous and intramuscular introduction. A typical daily dose of the active ingredient ranges from about 1 to 3000 mg, preferably to 300 mg, and can be administered in a single dose or in divided doses. However, it should be understood that the amount of the active ingredient actually administered should be determined in light of various relevant factors including the condition to be treated, the chosen route of administration, the age and weight of the individual patient, and the severity of the patient's symptoms; and, therefore, the dosage suggested above should not be construed to limit the scope of the invention in any way.

The following Reference Examples and Examples are intended to further illustrate the present invention without limiting its scope; and the experimental methods used in Examples are practiced in accordance with Reference Examples given hereinbelow unless otherwise stated.

Further, percentages given below for solid in solid mixture, liquid in liquid, and solid in liquid are on a wt/wt, vol/vol and wt/vol basis, respectively, unless specifically indicated otherwise.

REFERENCE EXAMPLE 1

Determination of CETP Inhibitory Activity

LDL and [$^3$H]-cholesteryl oleate-labelled HDL were synthesized in accordance with the method of Morton et al.(see, *J. Biol. Chem.*, 256, 11992–11995(1981)) and then separated using an ultracentrifuge(Beckman XL 70). LDL and [$^3$H]-HDL, thus prepared, were used as a CE-receptor and a CE-donor, respectively.

Pure CETP was separated from human blood plasma in accordance with the method of Hesler et al.(see, *J. Biol. Chem.*, 262, 2275–2282(1987)) and used as a CETP source.

0.3 ml of LDL, 0.05 ml of [$^3$H]-HDL and 0.05 ml of the CETP source, which were prepared above, and 0.05 ml of a CETP inhibitor were added into a 1.5 ml tube and reacted at 37° C. for 3 hours.

When the reaction was finished, LDL was precipitated in accordance with the method of Morton et al.(see, *Biochim. Biophys. Acta*, 663, 350–355(1981)). The amount of the isotope transferred to LDL was determined with a liquid scintillation counter(Packard Tricarb 1600 TR) using a part of the supernatant, and the activity of CETP was calculated therefrom.

The inhibitory activity of the CETP inhibitor was calculated from the CETP activities of the experimental group, in which the CETP inhibitor was added, and that of control group, in which no CETP inhibitor was added, as follows:

$$\mathit{CETP}\text{ inhibitory effect} = 1 - \frac{\mathit{CETP}\text{ activity of experimental group}}{\mathit{CETP}\text{ activity of control group}} \times 100$$

REFERENCE EXAMPLE 2

Quantification of Total Blood Cholesterol Level

Quantification of total blood cholesterol level in a rabbit was carried out in accordance with the method of Allain et al.(see, *Clinical Chemistry*, 20, 470–475(1974)). Specifically, 0.001 ml of rabbit blood plasma and 0.5 ml of enzyme reagent for determining cholesterol(Sigma 352-50) were added to a 1.5 ml tube and reacted at 37° C. for 5 min. with stirring. 0.2 ml of the reactant was taken and its O.D. at 500 nm was determined with a spectrometer. The concentration of total cholesterol was calculated by comparing the result with a standard curve.

REFERENCE EXAMPLE 3

Quantification of Blood HDL Cholesterol Level

Quantification of blood HDL cholesterol level in a rabbit was carried out in accordance with the dextran sulfate $MnCl_2$ precipitation method(see, Warnick et al., *Clinical Chemistry*, 28, 1385–1397(1982)). Specifically, 0.05 ml of rabbit blood plasma and 0.01 ml of HDL-cholesterol reagent (Sigma 352-3) were mixed, reacted, allowed to stand for 5 min. and then centrifuged at 3,000×g for 5 min. 0.005 ml of the supernatant was mixed with 0.5 ml of enzyme reagent for determining cholesterol(Sigma 352-50), and reacted at 37° C. for 5 min. with stirring. 0.2 ml of the reactant was taken and its O.D. at 500 nm was determined with a spectrometer. The concentration of HDL cholesterol was calculated by comparing the result with a standard curve.

EXAMPLE 1

Identification of CETP Inhibitory Peptide from Porcine Blood Plasma

The CETP inhibitory activities of human and porcine blood plasmas were determined in accordance with the procedures of Reference Example 1 using human and porcine blood plasmas as CETP inhibitors.

As a result, the porcine blood plasma showed a CETP inhibitory activity of about 10% compared to that of human plasma.

On the other hand, in accordance with the method of Morton et al., supra, the human and porcine plasmas were ultracentrifuged to obtain HDL fraction, which was then subjected to a polyacrylamide gel electrophoresis.

Figure 2:
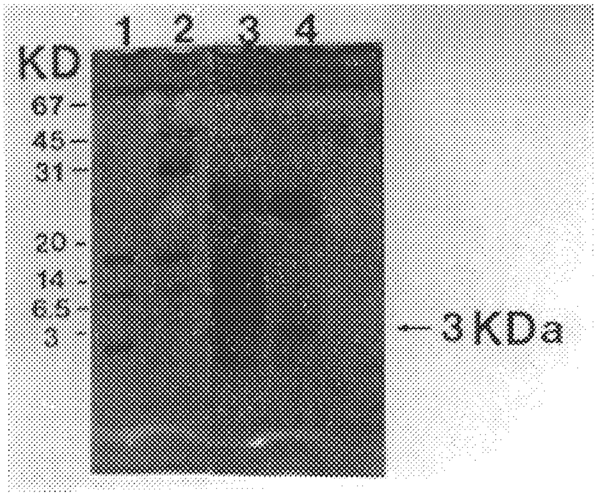
FIG. 2 depicts the result of an electrophoresis using HDL fractions of human and porcine blood plasmas.

FIG. 2 shows the result of electrophoresis using the HDL fractions of human and porcine plasmas, wherein lanes 1 and 2 are standard molecular weight markers, i.e., 67–14 kDa and 20–3 kDa, respectively, from the top of the gel; and lanes 3 and 4 are the HDL fractions of human and porcine plasmas, respectively.

As shown in FIG. 2, a protein band of about 3 kDa was observed in the porcine plasma only.

EXAMPLE 2

Separation of CETP Inhibitory Peptide from the Porcine Plasma 200 g of plasma was collected from fresh porcine blood and 10.5 g of ammonium sulfate was added thereto. The mixture was centrifuged at 4,000 rpm for 3 min. The supernatant was separated on a phenyl-Sepharose CL-4B column (Pharmacia, Sweden) and the CETP inhibitory activities of all the protein fractions were determined in accordance with the method of Reference Example 1.

The fractions having high CETP inhibitory activities were collected and then passed through a DEAE-Sephadex column(Pharmacia, Sweden) to collect the fractions having high CETP inhibitory activities. The fractions were then passed through a hydroxylapatite column(Bio-Rad, U.S.A.) to obtain a fraction containing 3 kDa peptide, whose CETP inhibitory activity was then determined in accordance with the method of Reference Example 1.

EXAMPLE 3

Determination of the CETP Inhibitory Activity of 3 kDa peptide

The 3 kDa protein band separated on the polyacrylamide gel as a result of electrophoresis in Example 1 was cut off with a surgical knife, added to an H-shaped tube of other electrophoresis apparatus, and then subjected to an electroelution(see, Hunkapiller et al., *Meth. Enzymol.*, 91, 227–236(1986)) to obtain a pure 3 kDa peptide.

Figure 3:
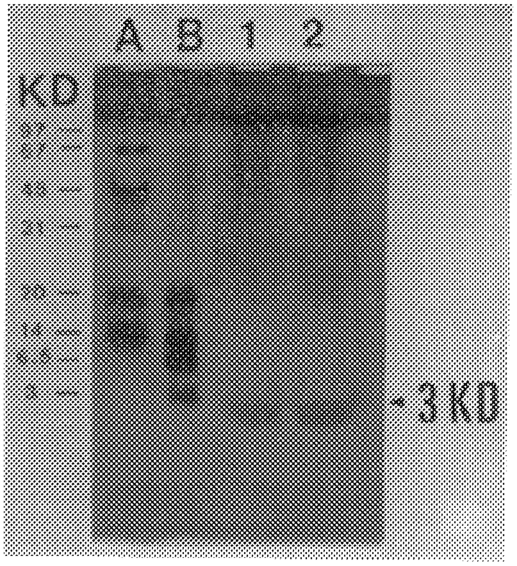
FIG. 3 displays the result of an electrophoresis using 3 kDa peptide of the present invention completely separated from porcine blood plasma.

FIG. 3 displays the result of the electrophoresis analyzing the 3 kDa peptide of the present invention completely separated from porcine blood plasma, wherein lanes A and B are standard molecular weight markers, i.e., 97–14 kDa and 20–3 kDa, respectively, from the top of the gel; lane 1 is the 3 kDa peptide electrophoresed with the addition of 0.2% β-mercaptoethanol which digests the disulfide bond; and lane 2 is the 3 kDa peptide electrophoresed without the addition of β-mercaptoethanol. As shown in FIG. 3, pure 3 kDa bands separated from the porcine blood plasma were confirmed in lanes 1 and 2, at the same position, which means that the peptide is of a single peptide.

CETP inhibitory activity of pure 3 kDa peptide thus separated or human albumin(as a control experiment) was determined in accordance with the method of the Reference Example. Further, the same procedures as in the Reference Example, except that human blood plasma itself was used as the CETP source, were repeated to determine CETP inhibitory activity of pure 3 kDa peptide.

Figure 4:
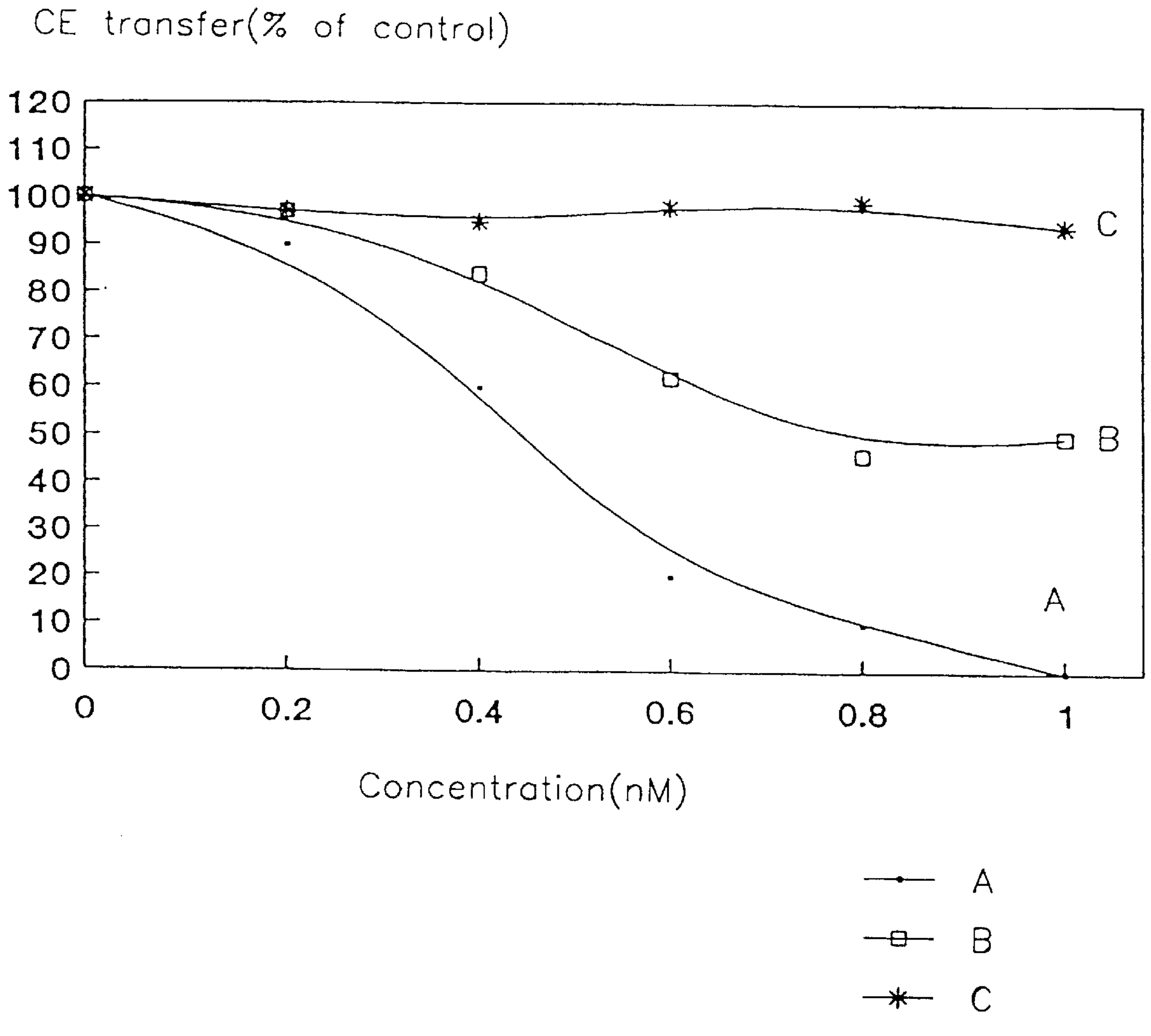
FIG. 4 exhibits the CETP inhibitory activity of 3 kDa peptide of the present invention.

FIG. 4 exhibits CETP inhibitory activity of 3 kDa peptide of the present invention, wherein curves A and B represent the CETP inhibitory activities of 3 kDa peptide, when pure CETP separated from human blood plasma and human blood plasma itself are used as CETP inhibitors, respectively; and curve C provides the CETP inhibitory activity of human albumin when pure CETP separated from human blood plasma is used as the CETP inhibitor. As shown in FIG. 4, human albumin hardly exhibits CETP inhibitory activity(C), while 1 nM of 3 kDa peptide shows CETP inhibitory activities of about 100% (A) and about 50% (B), when pure CETP separated from human blood plasma and human blood plasma itself are used as CETP inhibitors, respectively.

EXAMPLE 4

Amino Acid Sequencing of CETP Inhibitory Peptide

In accordance with the method of Laemmli et al.(see, *Nature*, 227, 680–685(1970)), 3 kDa peptide obtained in Example 2 was dissolved in a buffer(4% SDS, 0.25M Tris, 10% glycerol), reacted at 37° C. for 12 hours and then subjected to an electrophoresis at 15 mA on a 15% sodium dodecyl sulfate(SDS)-polyacrylamide gel.

In accordance with the method of Matsudaira(see, *J. Biol. Chem.*, 262, 10035–10038(1987)), 3 kDa peptide separated on the gel was transferred to a polyvinyl-difluoride(PVDF) membrane and the membrane was washed with 70% ethanol. 28 amino acids from the N-terminal of 3 kDa peptide was identified using an automated amino acid analyzer (Protein sequenator 470A, Applied Biosystem). As a result, the amino acid sequence was identified as follows:

Glu Asp Thr Ser Pro Glu Asp Lys Met Gln Asp Tyr Val Lys Gln Ala Thr Arg Thr Ala Gln Asp Ala Leu Thr Ser Val Lys . . . (SEQ ID NO: 1)

EXAMPLE 5

Synthesis of the CETP Inhibitory Peptide

On the basis of the amino acid sequence analyzed in Example 4, 3 kDa peptide having 28 amino acids($P_{28}$) was synthesized in a large quantity using an automated amino acid synthesizer employing a solid-phase bound method. Specifically, a C-terminal amino acid, whose amino group was protected with t-Boc group, was bound to a polystyrene resin, t-Boc group was eliminated therefrom and the next amino acid, whose amino group was also protected with t-Boc group, was bound to the unprotected amino group of the first amino acid through a peptide bond. This procedures were repeated until the 28th amino acid was bound to the growing peptide chain to synthesize Peptide $P_{28}$.

$P_{28}$ was separated from the polystyrene resin and purified using HPLC(GME 712, Gilson).

The same procedures as above were repeated to synthesize the peptides named as $P_{28'}$, $P_{13}$, $P_{10}$, $P_{18}$, $P_{24}$, $P_{20}$, $P_{14}$ and $P_8$, respectively, whose amino acid sequences were identified as follows:

$P_{28'}$:

Glu Asp Thr Ser Leu Leu Asp Lys Met Gin Asp Tyr Val Lys Gln Ala Thr Arg Thr Ala Gin Asp Ala Leu Thr Ser Val Lys . . . (SEQ ID NO: 2)

$P_{13}$:

Ser Glu Ala Glu Asp Ala Ser Leu Leu Ser Phe Met Gln . . . (SEQ ID NO: 3)

$P_{10}$:

Glu Asp Thr Ser Pro Glu Asp Lys Met Gln . . . (SEQ ID NO: 4)

$P_{18}$:

Glu Asp Thr Ser Leu Leu Asp Lys Met Gln Asp Tyr Val Lys Gln Ala Thr Arg . . . (SEQ ID NO: 5)

$P_{24}$:

Glu Asp Thr Ser Pro Glu Asp Lys Met Gln Asp Tyr Val Lys Gln Ala Thr Arg Thr Ala Gln Asp Ala Leu . . . (SEQ ID NO: 6)

$P_{20}$:

Glu Asp Thr Ser Pro Glu Asp Lys Met Gln Asp Tyr Val Lys Gln Ala Thr Arg Thr Ala . . . (SEQ ID NO: 7)

$P_{14}$:

Glu Asp Thr Ser Pro Glu Asp Lys Met Gln Asp Tyr Val Lys . . . (SEQ ID NO: 8)

$P_8$:

Glu Asp Thr Ser Pro Glu Asp Lys . . . (SEQ ID NO: 9)

EXAMPLE 6

CETP Inhibitory Activities of the Synthesized Peptides

CETP inhibitory activities of peptides $P_{28}$, $P_{10}$, $P_{18}$, $P_{24}$, $P_{20}$ and $P_{14}$ were determined in accordance with the method of Reference Example 1 using pure CETP or human blood plasma as a CETP source. To exclude possible nonspecific inhibition, a 2 kDa soluble peptide having an optional amino acid sequence was synthesized, and CETP inhibitory activity thereof was determined in a similar manner(control group). The result of the above experiment is shown in Table I.

TABLE I

| Peptide | Final Conc. of Peptide (μM) | CETP Source | Inhibitory Activity (Mean ± S.D.) | Number of Experiments |
|---|---|---|---|---|
| $P_{28}$ | 2 | pure CETP | 100 ± 1.7 | 5 |
| | | human plasma | 50 ± 3.2 | 5 |
| $P_{10}$ | 2 | pure CETP | 100 ± 2.0 | 5 |
| | | human plasma | 50 ± 4.5 | 5 |
| $P_{18}$ | 2 | pure CETP | 90 ± 3.5 | 5 |
| | | human plasma | 40 ± 5.5 | 5 |
| $P_{24}$ | 2 | pure CETP | 100 ± 2.5 | 5 |
| | | human plasma | 50 ± 0.8 | 5 |
| $P_{20}$ | 2 | pure CETP | 90 ± 1.5 | 5 |
| | | human plasma | 45 ± 2.2 | 5 |
| $P_{14}$ | 2 | pure CETP | 50 ± 3.5 | 5 |
| | | human plasma | 15 ± 1.5 | 5 |
| 2kDa Peptide (control group) | 2 | pure CETP | 0.3 ± 0.3 | 5 |
| | | human plasma | 0.4 ± 0.3 | 5 |

In Table I, inhibitory activity of the peptides is expressed by the mean ± standard deviation through variance analysis, and the results showing significant errors were examined by Duncan's Multiple Range Test(see, Duncan, D. B., "Multiple Range and Multiple F Test", *Biometrics*, 11, 1–12 (1955)).

As can be seen from Table I, Peptides $P_{28}$ and $P_{10}$, and their fragments, i.e., Peptides $P_{10}$, $P_{18}$, $P_{24}$ and $P_{20}$, exhibit high CETP inhibitory activities, i.e., about 90–100% against pure CETP and about 40–50% against human blood plasma.

The 2 kDa peptide used as a control group had little effect on the transfer of CE from HDL to LDL.

EXAMPLE 7

CETP Inhibitory Activities of the Synthesized Peptides

Peptides $P_{24}$, $P_{20}$ and $P_{14}$ were expressed in *E. coli* in accordance with conventional genetic engineering techniques, and CETP inhibitory activities thereof were determined in accordance with the method of Reference Example using human blood plasma as a CETP source. The result is shown in Table II, where all of peptides $P_{24}$, $P_{20}$ and $P_{14}$ exhibits CETP inhibitory activities.

TABLE II

| CETP Inhibitor | Conc. of inhibitor (μM) | CETP Source | Inhibitory Activity (Mean ± SD) | Number of Experiments |
|---|---|---|---|---|
| Peptide $P_{24}$ | 2 | human plasma | 50 ± 0.8 | 3 |
| Peptide $P_{20}$ | 2 | human plasma | 45 ± 2.2 | 3 |
| Peptide $P_{14}$ | 2 | human plasma | 15 ± 1.5 | 3 |

EXAMPLE 8

Confirmation of the Amino Acid Affecting CETP Inhibitory Activity

To verify the amino acid, which directly affects CETP inhibitory activity of Peptide $P_{10}$ whose CETP inhibitory activity was confirmed in Example 6, each of the amino acid residues of $P_{10}$ was substituted by turns with an alanine residue to obtain ten variants thereof.

CETP inhibitory activities of the variants were determined in accordance with the method of Reference Example and the result is shown in Table III.

TABLE III

| Variants | Position of substituted amino acid | Final Conc. (μM) | CETP inhibitory activity | Number of experiments |
|---|---|---|---|---|
| A | 1st | 7 | −12 | 3 |
| B | 2nd | 7 | −15 | 3 |
| C | 3rd | 8 | −6 | 3 |
| D | 4th | 7 | −12 | 3 |
| E | 5th | 9 | −6 | 3 |
| F | 6th | 6 | 29 | 3 |
| G | 7th | 2 | −3 | 3 |
| H | 8th | 5 | 5 | 3 |
| I | 9th | 9 | 69 | 3 |
| J | 10th | 7 | 41 | 3 |

As shown in Table III, the 1st to the 5th amino acids from the N-terminal of $P_{10}$ were found to be critical to CETP inhibitory activity, and the 9th and the 10th amino acids were verified to have little influence on the activity of $P_{10}$.

EXAMLPE 9

CETP Inhibitory Activity of Peptide $P_{28}$ According to a Substrate

In order to identify the inhibitory mechanism of Peptide $P_{28}$ in blood, CETP inhibitory activity of Peptide $P_{28}$ was determined in accordance with the method of Reference Example 1, using VLDL, LDL, HDL or re-synthesized LDL(LDLR) as a CE-receptor. LDLR was synthesized from LDL obtained in Reference Example 1 by the method of Morton et al.(see, *J. Biol. Chem.*, 256, 11992–11995(1981)). The LDL was delipidated with chloroform and subjected to a gel chromatography to obtain ApoB100 protein. Phosphatidylcholine and cholesteryl oleate was thoroughly mixed, dried using nitrogen gas, and ApoB100 protein obtained above was added thereto. The mixture was reacted with stirring, dialyzed against tris buffer, and subjected to a gel chromatography to obtain LDLR.

Figure 5:
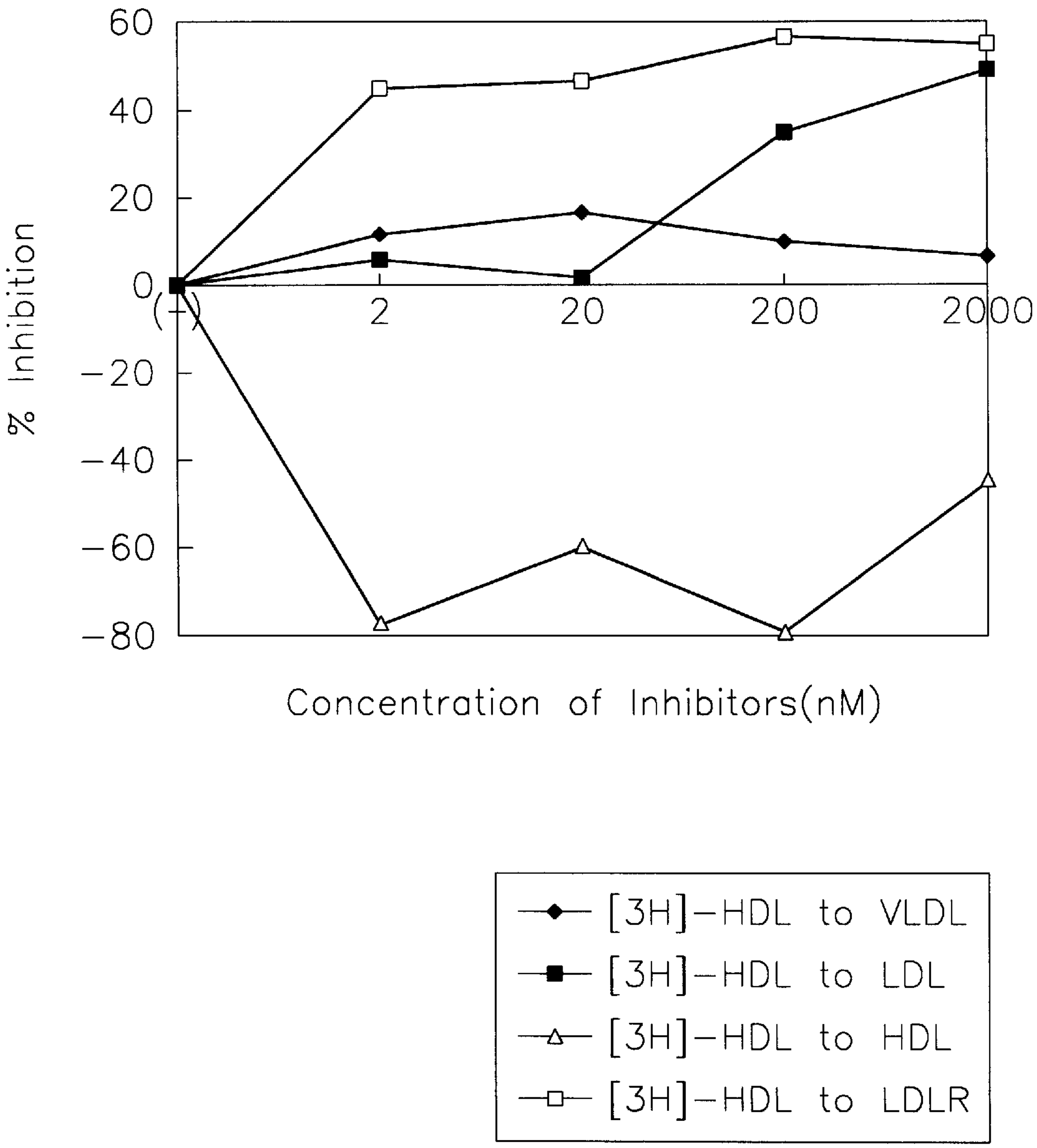
FIG. 5 describes the CETP inhibitory activity of Peptide $P_{28}$ according to the substrates.

The result is shown in FIG. 5, wherein Peptide $P_{28}$, in a final concentration of 2 μM, can be found to inhibit the transfer of CE from HDL to VLDL by about 10%; from HDL to LDL, by 50%; and from HDL to LDLR, by 55%. Inhibition of CE transfer from HDL to HDL by Peptide $P_{28}$ was not observed.

EXAMPLE 10

Toxicity Test

Human fibroblast cell line(A431, ATCC CRL 1555) was cultured on DMEM medium containing 10% fetal bovine serum(FBS), with the addition of 10% (wt/vol) Peptide $P_{28}$, $P_{18}$, $P_{10}$, $P_{24}$, $P_{20}$ or $P_{14}$, for 72 hours. The cultured cells showed no change in their growth condition and morphology, when compared with a control group cultured without any of the peptides.

EXAMPLE 11

In vivo Test for the Effect of the Peptides

The effects of peptides $P_{28}$ and $P_{10}$ on lipoprotein metabolism in an animal were examined by using 4 groups of New Zealand white rabbits having induced hyperlipemia by injecting peptides thereinto. The experimental conditions were as shown in Table IV.

TABLE IV

| Group | Feed | Injection | Conc. of Cholesterol just before injection (mg/dl)[1] |
|---|---|---|---|
| A (n = 7)[2] | Purina ®[3] | Physiological Saline | 64 |
| B (n = 6) | Purina ® (0.3% cholesterol added) | Physiological Saline | 297 |
| C (n = 6) | Purina ® (0.3% cholesterol added) | Peptide $P_{10}$ 20 mg | 307 |
| D (n = 7) | Purina ® (0.3% cholesterol added) | Peptide $P_{28}$ 20 mg | 302 |

Notes:
[1]Average cholesterol concentration in each group
[2]Number of rabbits in each group
[3]Purina ® Feed: Purina Co. (No. 5321)

The rabbits of Groups B, C and D were fed with 0.3% cholesterol diet for 3 weeks before injection to induce hyperlipidemia. The rabbits of Groups A or B were injected with 1 ml of physiological saline through their otic veins, and the rabbits of groups C and D were injected with 20 mg of each of Peptide $P_{28}$ and $P_{10}$, respectively, in the same manner. 2 ml each of blood was taken from the rabbits through their otic veins for 72 hours at every 1, 3 or 6 hours from the injection. The blood plasma was separated from the blood in accordance with the method of Reference Example 2 and stored at a freezer of −20° C. until be used. After the exsanguination was completed, the effects of Peptides $P_{28}$ and $P_{10}$ were examined on following 3 items, and the results were as follows:

1. Effect of Peptides $P_{28}$ and $P_{10}$ on CETP activity

Figure 6:
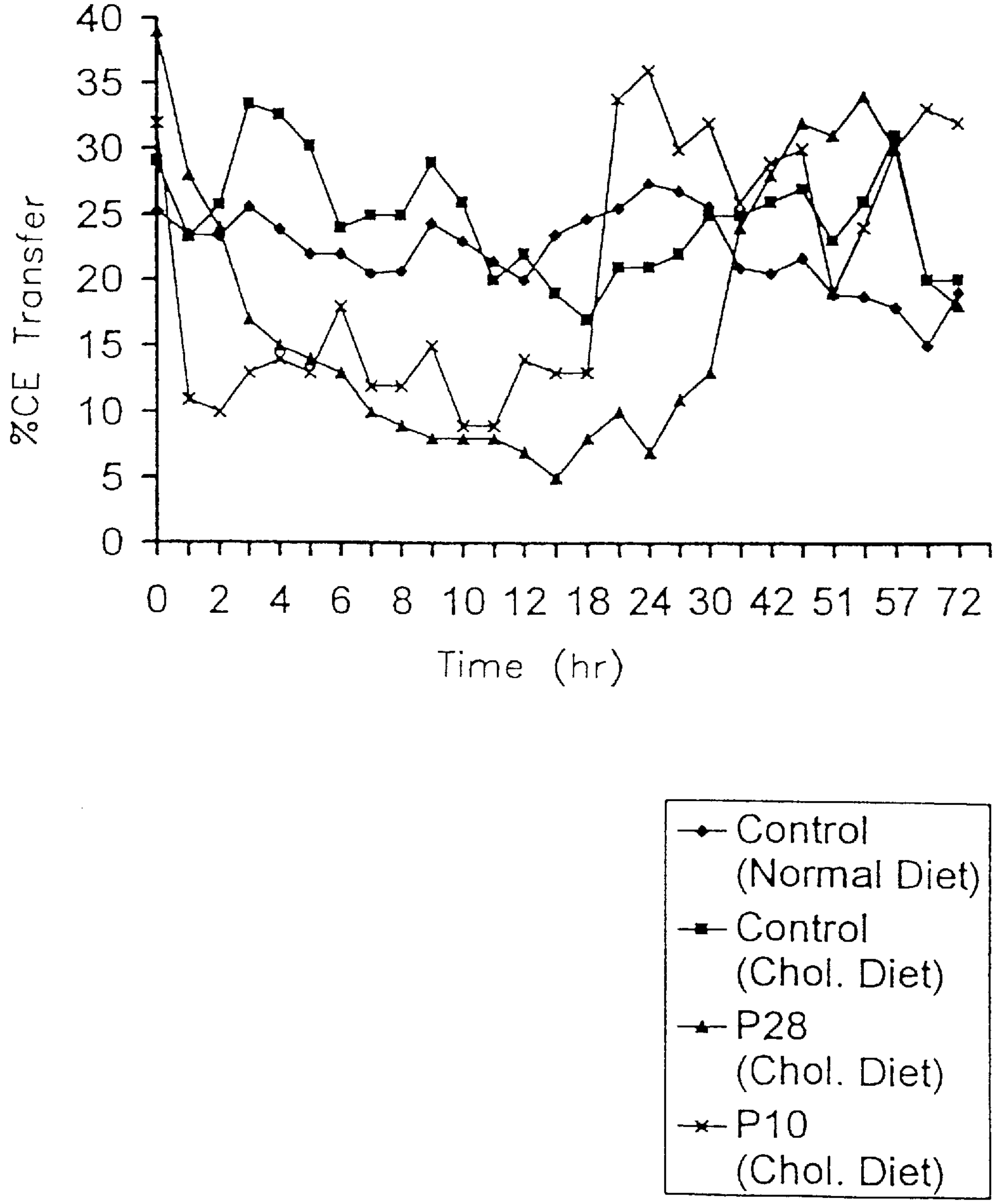
FIG. 6 illustrates the effect of Peptides $P_{28}$ and $P_{10}$ on the CETP activity in a rabbit.

Blood samples were taken from rabbits just before the intravenous injection and for 72 hours after the injection at every hour, and the CETP activities thereof were determined in accordance with the method of Reference Example 1. As a result, little changes in CETP activities were observed in groups A and B for 72 hours after the injection. Group C exhibited more than 70% of CETP inhibitory activity when compared to the control group, i.e., group B, until 30 hours after the injection. Group D exhibited more than 60% of inhibitory activity, when compared to group B, until 20 hours after the injection. The results are shown in FIG. 6.

Figure 7:
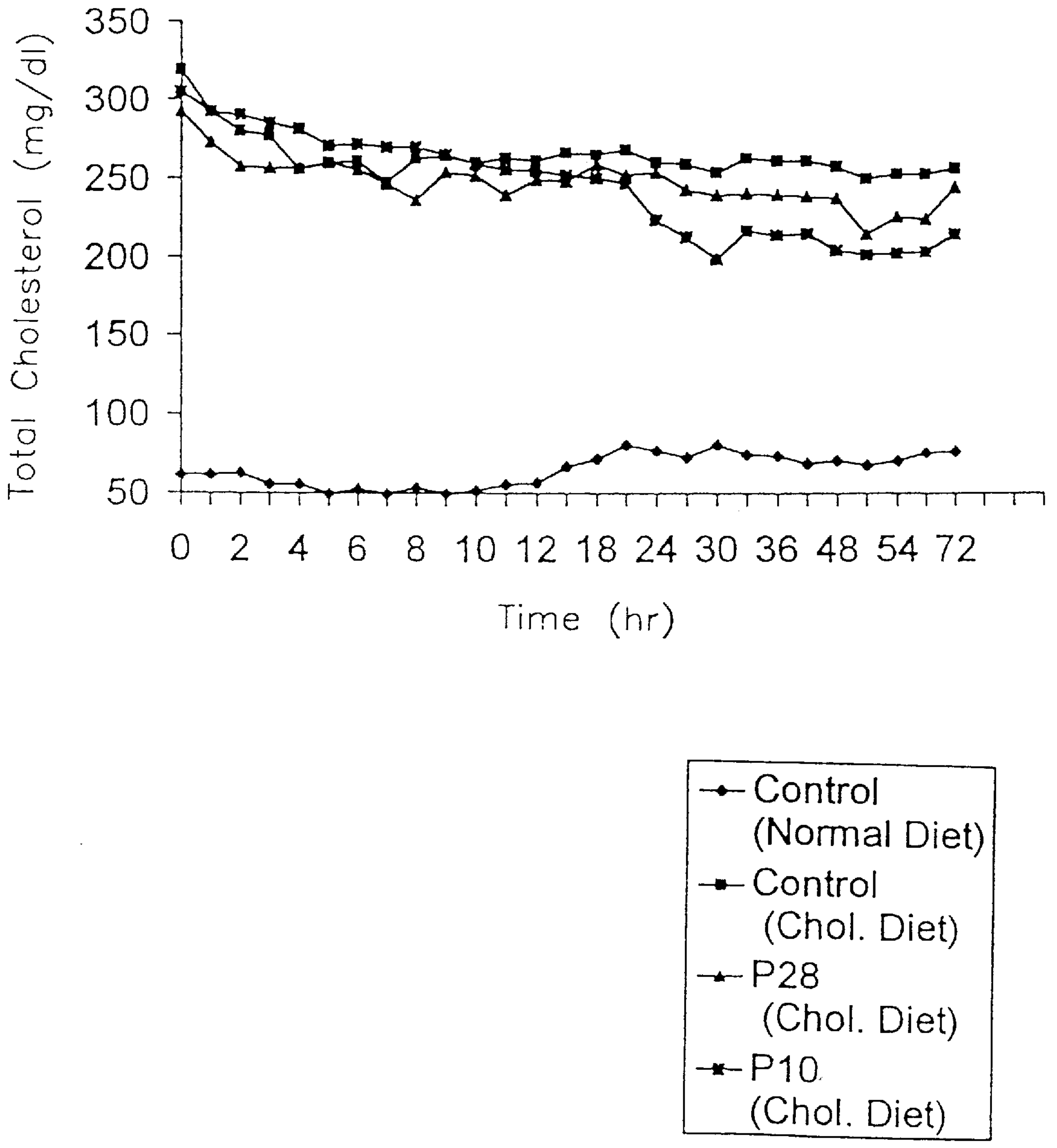
FIG. 7 represents the effect of Peptides $P_{28}$ and $P_{10}$ on the total blood cholesterol level in a rabbit.

2. Effect of Peptides $P_{28}$ and $P_{10}$ on the total blood cholesterol level Blood samples were taken from rabbits just before the intravenous injection and for 72 hours after the injection at every hour, and the changes in the total blood cholesterol levels were examined in accordance with the method of Reference Example 2. As a result, the total blood cholesterol level in the rabbit of group A slightly decreased at initial stage, and slowly increased after 20 hours from the injection; and in group B, decreased 5% right after the injection but became stable after 7 hours from the injection. However, in groups C and D, the levels decreased right after the injection and became 80% of the initial level after 9 hours from the injection in case of group C, and 70% of the initial level after 12 hours from the injection in case of group D. The results are shown in FIG. 7.

3. Effect of Peptides $P_{28}$ and $P_{10}$ on blood HDL cholesterol level

Figure 8:
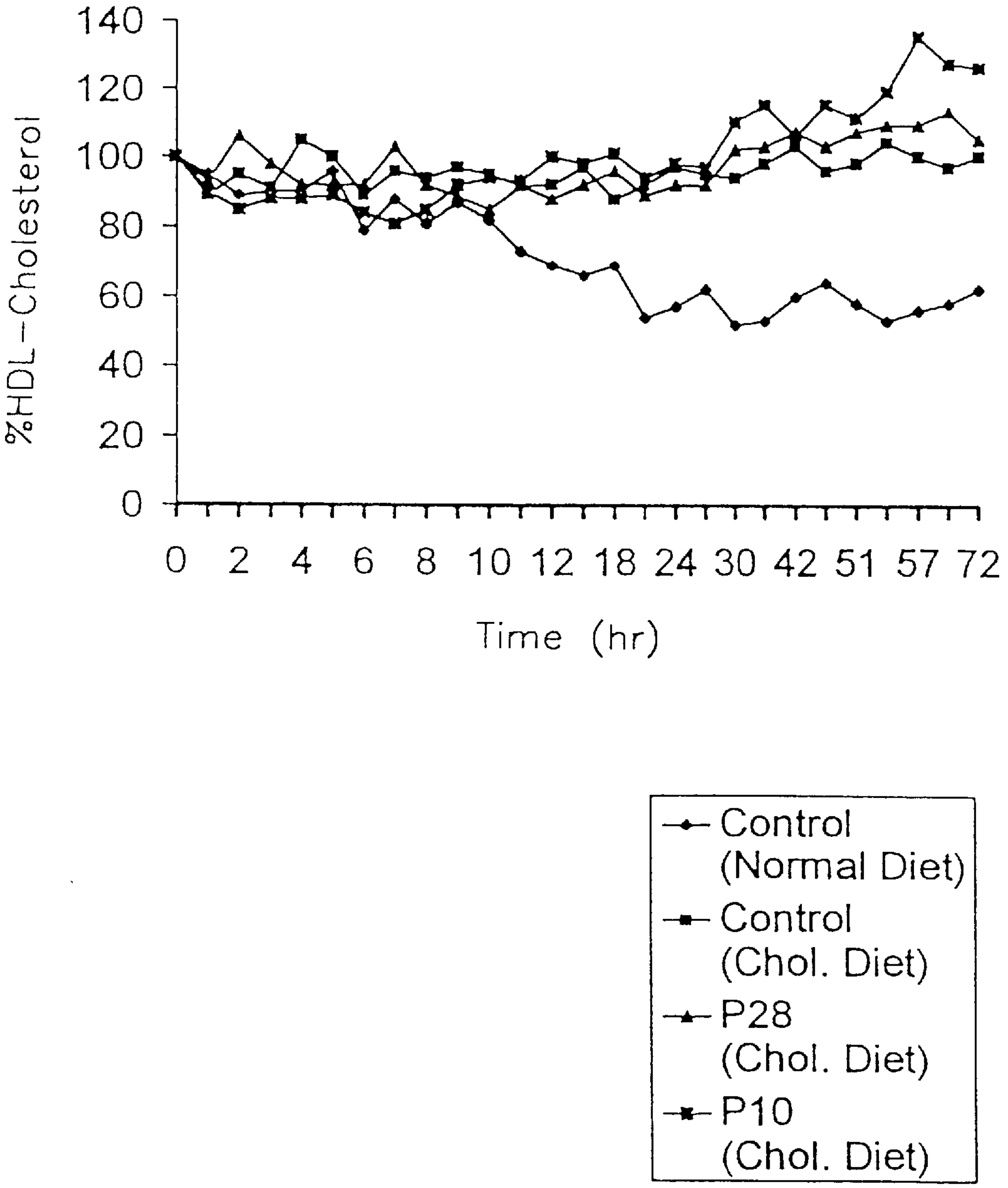
FIG. 8 presents the effect of Peptides $P_{28}$ and $P_{10}$ on the blood HDL cholesterol level in a rabbit.

Blood samples were taken from rabbits just before the intravenous injection and for 72 hours after the injection at a regular interval, and the changes in the blood HDL cholesterol levels were examined in accordance with the method of Reference Example 3. As a result, in group A, the blood HDL cholesterol level slightly decreased right after the injection; in group B, maintained at a constant level; in group C, gradually increased at 30 hours from the injection and increased upto 113% of the initial level at 36 hours from the injection; and in group D, gradually increased right after the injection and increased to 135% of the initial level at 57 hours from the injection. The results are shown in FIG. 8.

EXAMPLE 12

Production of an Antibody Specific for Peptide $P_{28}$ or $P_{10}$

Figure 9:
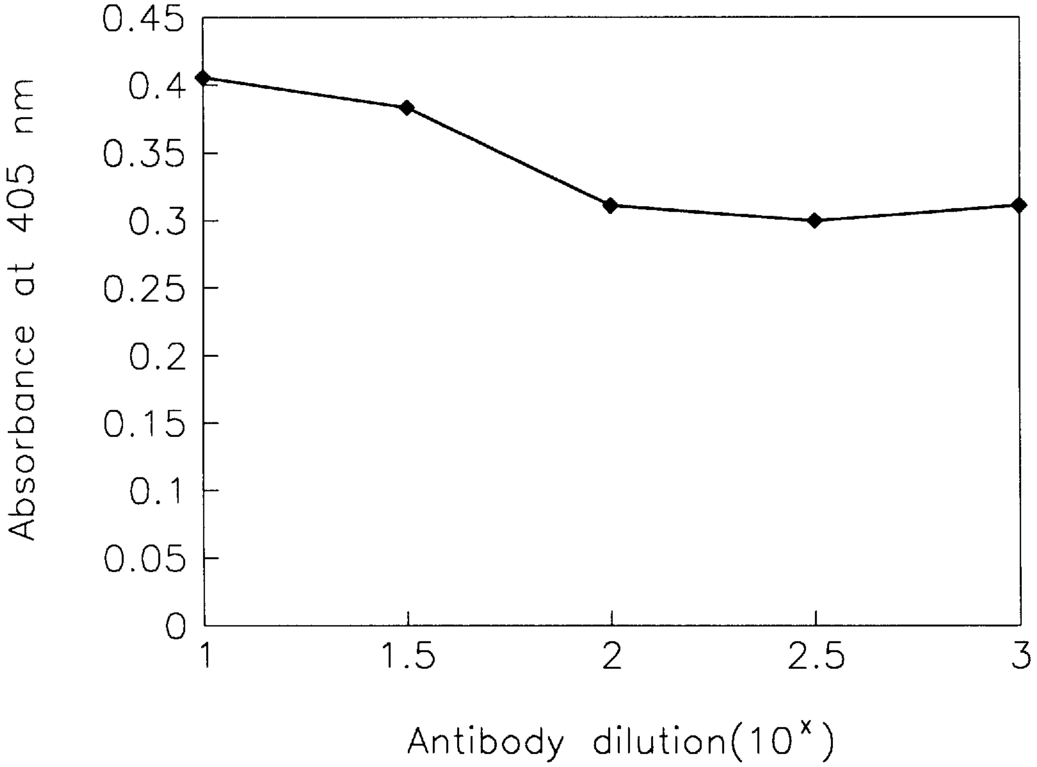
FIG. 9 exemplifies the production of antibodies having a specificity for Peptide $P_{28}$ or $P_{10}$.

An Antibody specific for Peptide $P_{28}$ or $P_{10}$ was produced as follows. In order to increase the immunogenicity of the peptide, it was conjugated with key-hole limpet hemocyanin (KLH) by employing a conjugation kit(Pierce 77101, France). The conjugated peptide was mixed thoroughly with an equal volume of Freund's complete adjuvant(FCA, Sigma F5881, U.S.A.), which were injected subcutaneously into the rabbits. Four additional injections were carried out at every 2 weeks using a mixture of the conjugated peptide and Freund's incomplete adjuvant(Sigma F5506, U.S.A.). After the final injection, a blood sample was taken from the otic vein of a rabbit and the antibody titer thereof was examined by ELISA test to confirm the production of antibodies against Peptides $P_{28}$ and $P_{10}$. The results are shown in FIG. 9. 30 ml of the blood samples, which was confirmed for the production of antibodies were taken from a rabbit to obtain an antiserum against Peptides $P_{28}$ and $P_{10}$, and the antiserum was passed through Protein A column (Pierce 22811, France) to produce immunoglobulin G(IgG) specific for Peptides $P_{28}$ and $P_{10}$.

EXAMPLE 13

Analogues of Peptide $P_{10}$

Peptide $P_{10}$ was dissolved in a carbonate buffer(pH 9.5) to a final concentration of 1 μg/ml. The resulting solution was added to the wells of an ELISA plate(Nunc, U. S. A.) in an amount of 100 $\mu$l/well and reacted at 4° C. for 18 hours to have the peptide adsorbed onto the plate. The plate was washed three times with a phosphate buffer(pH 7.2); and 0.2% gelatin solution was added to the wells in an amount of 200 $\mu$l/well, and reacted at room temperature for 2 hours to block the remaining protein adsorption sites.

100 $\mu$l of a solution containing an antibody against Peptide $P_{10}$ diluted with 100,000-fold volume of phosphate bufferred saline(PBS, pH 7.2) or 100 $\mu$l of the antibody solution further containing 1 $\mu$g of each of the Peptide $P_{10}$ variants, i.e., variants E(A5) and J(A10) obtained in Example 8 and variant D10, wherein the 10th amino acid has a D-configuration, was added to the wells of the plate. The plate was reacted at 37° C. for 2 hours and washed three times with a phosphate buffer(pH 7.2).

A solution comprising anti-mouse IgG antibody labelled with horseradish peroxidase(HRP) which was diluted with 10,000-fold volume of PBS(pH 7.2) was added to the wells in an amount of 100 $\mu$l/well. The resultant was incubated at 37° C. for 2 hours and washed three times with phosphate buffer(pH 7.2). Thereafter, 100 $\mu$l of O-phenylene diamine (OPD, Sigma, U.S.A.) solution was added to each well and incubated at room temperature for 30 minutes in the dark. To the resultant was added 150 $\mu$l/well of 2N sulfuric acid to stop the color development; and O.D. of each well was determined at 492 nm with an ELISA reader(Dynatech MR 5000, U.S.A.).

Figure 10:
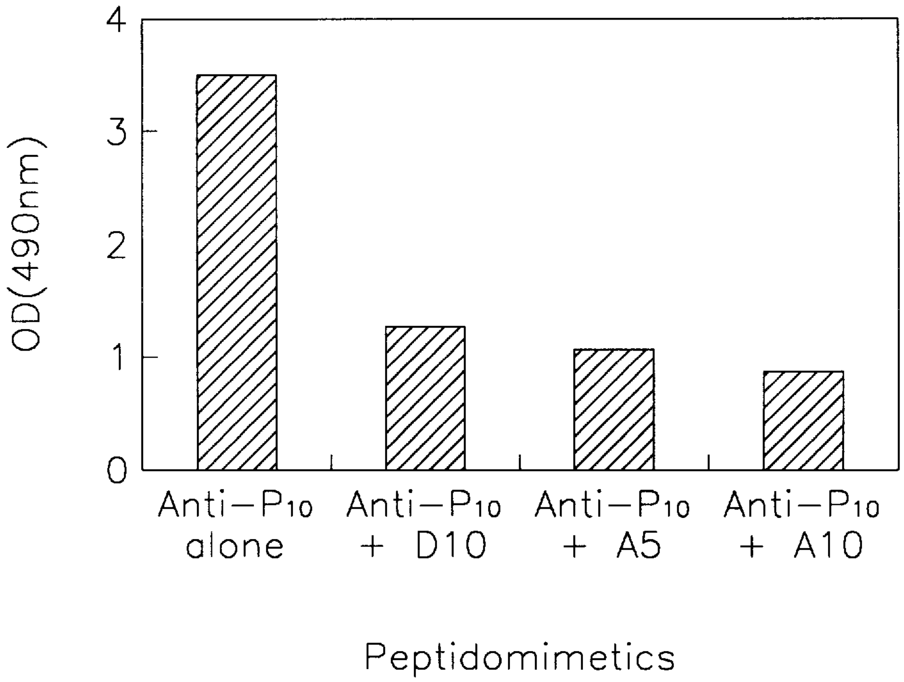
FIG. 10 indicates the inhibition of binding of Peptide $P_{10}$ to an antibody having a specificity therefor by variants of Peptide $P_{10}$.

As shown in FIG. 10, the three variants, i.e., A5, A10 and D10, which have CETP inhibitory activity as described in Example 8, inhibited the binding of Peptide $P_{10}$ to its antibody.

EXAMPLE 14

Determination of the CETP Inhibitory Activity of Porcine and Human Apo CIII Fragments Two N-terminal fragments of porcine and human apo-CIIIs, i.e., Peptides $P_{28'}$, and $P_{13}$, which are highly homologous in their amino acid sequences with Peptide $P_{10}$ having CETP inhibitory activity, was produced in *E. coli* using genetic engineering techniques. The amino acid sequences of Peptides $P_{28'}$, and $P_{13}$ are as follows:

$P_{28'}$:

Glu Asp Thr Ser Leu Leu Asp Lys Met Gln Asp Tyr Val Lys Gln Ala Thr Arg Thr Ala Gln Asp Ala Leu Thr Ser Val Lys . . . (SEQ ID NO: 2)

$P_{13}$:

Ser Glu Ala Glu Asp Ala Ser Leu Leu Ser Phe Met Gln . . . (SEQ ID NO: 3)

CETP inhibitory activity of Peptides $P_{28'}$ and $P_{13}$ was determined in accordance with the method of Reference Example 1, except that human blood plasma was used as the CETP source. The result is shown in Table V.

TABLE V

| Peptide | Final Conc. of Peptide ($\mu$M) | CETP source | Inhibitory Activity | Number of Experiments |
|---|---|---|---|---|
| $P_{10}$ | 2 | human plasma | 45 ± 2.3 | 3 |
| $P_{28'}$ | 2 | human plasma | 32 ± 3.8 | 3 |
| $P_{13}$ | 2 | human plasma | 34 ± 2.9 | 3 |

As shown in Table V, the N-terminal fragments of porcine and human apo-CII, i.e., Peptides $P_{28'}$ and $P_{13}$ exhibit CETP inhibitory activity.

While the invention has been described with respect to the above specific embodiments, it should be recognized that various modifications and changes may be made to the invention by those skilled in the art which also fall within the scope of the invention as defined by the appended claims.

What is claimed is:

1. A peptide consisting of the amino acid sequence of SEQ ID NO: 1, which has an inhibitory activity on cholesteryl ester transfer protein.

2. A fragment of the peptide of claim 1, which comprises the 1st to the 6th amino acids of the N-terminus of the peptide of claim 1.

3. The fragment of claim 2, which has an amino acid sequence selected from the group consisting of: SEQ ID NO: 4, SEQ ID NO: 6, SEQ ID NO: 7, SEQ ID NO: 8 and SEQ ID NO: 9.

4. An analogue of the peptide of claim 1, wherein at least one amino acid is substituted with a modified amino acid selected from the group consisting of:

2-amino adipic acid, Asp or $C_a$-methylGlu for Glu;

Glu, $C_a$-methylAsp or β-carboxyAsp for Asp;

Ser or $C_a$-methylThr for Thr;

Thr or $C_a$-methylSer for Ser;

3,4-dehydroPro or $C_a$-methylPro for Pro;

ornithine, citrulline, Arg or $C_a$-methylLys for Lys;

$C_a$-methylMet for Met;

Asn, citrulline or $C_a$-methylGln for Gln;

isoVal, norval, $C_a$-methylVal or Leu for Val;

Gly, β-Ala, $C_a$- methylAla or 2-aminobutyric acid for Ala;

Lys, homoArg, $C_a$-methylArg or citrulline for Arg; and norleu, isoleu or $C_a$-methylLeu for Leu.

5. An analogue of the peptide of claim 1, wherein at least one peptide bond thereof is replaced with a thioether bond ($—CH_2—S—$), an alkyl bond($—CH_2—CH_2—$) or an amino bond($—CH_2—NH_2—$), with the amino-terminal thereof being acetylated or the carboxy-terminal thereof being amidated.

6. A composition for inhibiting the activity of cholesteryl ester transfer protein, comprising an effective amount of the peptide of claim 1 and a pharmaceutically acceptable carrier.

7. A process for preparing the peptide of claim 1, comprising the steps of:

(a) mixing porcine blood plasma with ammonium sulfate, (b) centrifuging the mixture obtained in step (a) to obtain a supernatant, (c) subjecting the supernatant obtained in step (b) to hydrophobic interaction column chromatography to obtain fractions having an inhibitory activity on cholesterol ester transfer protein(CETP), (d) subjecting the fractions obtained in step (c) to anion exchange column chromatography to obtain fractions having a high inhibitory activity on CETP, and (e) subjecting the fractions obtained in step (d) to hydroxyapatite column chromatography to obtain a fraction containing the peptide of claim 1.

8. A method for inhibiting the activity of cholesteryl ester transfer protein in a human subject, which comprises administering to the subject an inhibitorily effective amount of a peptide selected from the group consisting of: SEQ ID NO: 1, SEQ ID NO: 4, SEQ ID NO: 6, SEQ ID NO: 7, SEQ ID NO: 8 and SEQ ID NO: 9.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
( A ) LENGTH: 28 amino acids
( B ) TYPE: amino acid
( D ) TOPOLOGY: linear ( i i ) MOLECULE TYPE: protein ( i x ) FEATURE: peptide P28

( x i ) SEQUENCE DESCRIPTION: SEQ ID NO: 1:

```
Glu Asp Thr Ser Pro Glu Asp Lys Met Gln Asp Tyr Val Lys Gln
1               5                   10                  15

Ala Thr Arg Thr Ala Gln Asp Ala Leu Thr Ser Val Lys
                20                  25
```

( 2 ) INFORMATION FOR SEQ ID NO: 2:

( i ) SEQUENCE CHARACTERISTICS:
( A ) LENGTH: 28 amino acids
( B ) TYPE: amino acid
( D ) TOPOLOGY: linear ( i i ) MOLECULE TYPE: protein ( i x ) FEATURE: peptide P28'

( x i ) SEQUENCE DESCRIPTION: SEQ ID NO: 2:

Glu Asp Thr Ser Leu Leu Asp Lys Met Gln Asp Tyr Val Lys Gln
1 5 10 15

Ala Thr Arg Thr Ala Gln Asp Ala Leu Thr Ser Val Lys
20 25

( 2 ) INFORMATION FOR SEQ ID NO: 3:

( i ) SEQUENCE CHARACTERISTICS:
( A ) LENGTH: 13 amino acids
( B ) TYPE: amino acid
( D ) TOPOLOGY: linear ( i i ) MOLECULE TYPE: protein ( i x ) FEATURE: peptide P13

( x i ) SEQUENCE DESCRIPTION: SEQ ID NO: 3:

Ser Glu Ala Glu Asp Ala Ser Leu Leu Ser Phe Met Gln
1 5 10

( 2 ) INFORMATION FOR SEQ ID NO: 4:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( i x ) FEATURE: peptide P10

( x i ) SEQUENCE DESCRIPTION: SEQ ID NO: 4:

Glu Asp Thr Ser Pro Glu Asp Lys Met Gln
1 5 10

( 2 ) INFORMATION FOR SEQ ID NO: 5:

( i ) SEQUENCE CHARACTERISTICS:
( A ) LENGTH: 18 amino acids
( B ) TYPE: amino acid
( D ) TOPOLOGY: linear ( i i ) MOLECULE TYPE: protein ( i x ) FEATURE: peptide P18

( x i ) SEQUENCE DESCRIPTION: SEQ ID NO: 5:

Glu Asp Thr Ser Leu Leu Asp Lys Met Gln Asp Tyr Val Lys Gln
1 5 10 15

Ala Thr Arg ( 2 ) INFORMATION FOR SEQ ID NO: 6:

( i ) SEQUENCE CHARACTERISTICS:
( A ) LENGTH: 24 amino acids
( B ) TYPE: amino acid
( D ) TOPOLOGY: linear ( i i ) MOLECULE TYPE: protein ( i x ) FEATURE: peptide P24

( x i ) SEQUENCE DESCRIPTION: SEQ ID NO: 6:

Glu Asp Thr Ser Pro Glu Asp Lys Met Gln Asp Tyr Val Lys Gln
1 5 10 15

Ala Thr Arg Thr Ala Gln Asp Ala Leu
20

( 2 ) INFORMATION FOR SEQ ID NO: 7:

( i ) SEQUENCE CHARACTERISTICS:
( A ) LENGTH: 20 amino acids
( B ) TYPE: amino acid
( D ) TOPOLOGY: linear ( i i ) MOLECULE TYPE: protein ( i x ) FEATURE: peptide P20

( x i ) SEQUENCE DESCRIPTION: SEQ ID NO: 7:

Glu Asp Thr Ser Pro Glu Asp Lys Met Gln Asp Tyr Val Lys Gln
1 5 10 15

Ala Thr Arg Thr Ala
20

( 2 ) INFORMATION FOR SEQ ID NO: 8:

( i ) SEQUENCE CHARACTERISTICS:
( A ) LENGTH: 14 amino acids
( B ) TYPE: amino acid
( D ) TOPOLOGY: linear ( i i ) MOLECULE TYPE: protein ( i x ) FEATURE: peptide P14

( x i ) SEQUENCE DESCRIPTION: SEQ ID NO: 8:

Glu Asp Thr Ser Pro Glu Asp Lys Met Gln Asp Tyr Val Lys
1 5 10

( 2 ) INFORMATION FOR SEQ ID NO: 9:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( i x ) FEATURE: peptide P8

( x i ) SEQUENCE DESCRIPTION: SEQ ID NO: 9:

Glu Asp Thr Ser Pro Glu Asp Lys
1 5

( 2 ) INFORMATION FOR SEQ ID NO: 10:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( i x ) FEATURE: peptide P10 analogue ( x i ) SEQUENCE DESCRIPTION: SEQ ID NO: 10:

-continued

Glu Asp Thr Ser Ala Glu Asp Lys Met Gln
1 5 10

( 2 ) INFORMATION FOR SEQ ID NO: 11:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( i x ) FEATURE: peptide P10 analogue ( x i ) SEQUENCE DESCRIPTION: SEQ ID NO: 11:

Glu Asp Thr Ser Pro Glu Asp Lys Met Ala
1 5 10

( 2 ) INFORMATION FOR SEQ ID NO: 12:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( i x ) FEATURE: peptide P10 analogue ( x i ) SEQUENCE DESCRIPTION: SEQ ID NO: 12:

Glu Asp Thr Ser Pro Glu Asp Lys Met Xaa
1 5 10